United States Patent [19]

Shinohara et al.

[11] Patent Number: 5,227,504
[45] Date of Patent: Jul. 13, 1993

[54] TRIALKYLSILYLATING AGENT AND PROCESS FOR PREPARING N,N-DISUBSTITUTED AMINOTRIALKYLSILANE USING THE SAME

[75] Inventors: Toshio Shinohara, Takasaki; Muneo Kudo; Kazuyuki Matsumura, both of Annaka, all of Japan

[73] Assignee: Shin-Etsu Chemical Co., Ltd., Tokyo, Japan

[21] Appl. No.: 882,898

[22] Filed: May 14, 1992

[30] Foreign Application Priority Data

May 14, 1991 [JP] Japan .................................. 3-138478

[51] Int. Cl.$^5$ ................................................ C07F 7/10
[52] U.S. Cl. ............................... 556/411; 556/413; 556/419
[58] Field of Search ....................... 556/411, 413, 419

[56] References Cited

U.S. PATENT DOCUMENTS 4,739,088  4/1988  Endres et al. .................... 556/411
5,021,600  6/1991  Cardinali et al. ................ 556/411

Primary Examiner—Paul F. Shaver
Attorney, Agent, or Firm—Oblon, Spivak, McClelland, Maier & Neustadt

[57] ABSTRACT

A silylating agent comprising an N-(trialkylsilyl)benzanilide having the following general formula:

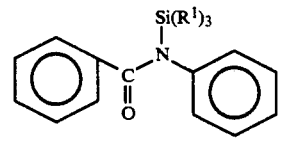

wherein $R^1$ is a lower alkyl group. This agent is reacted with a secondary amine to produce an N,N-dialkylaminotrialkylsilane. This process is free of formation of amine hydrochlorides as by-products. Therefore, the problem associated with disposal of such amine hydrochlorides and the problem of limitations on the use of the silane compound product due to mixing of such amine hydrochlorides can be obviated effectively.

5 Claims, No Drawings

TRIALKYLSILYLATING AGENT AND PROCESS FOR PREPARING N,N-DISUBSTITUTED AMINOTRIALKYLSILANE USING THE SAME

BACKGROUND OF THE INVENTION

1. Field of the Invention

This invention relates to a trialkylsilylating agent comprising an N-(trialkylsilyl)benzanilide, and more particularly to a process for preparing an N,N-disubstituted aminotrialkylsilane by use of the silylating agent.

2. Description of the Prior Art

Heretofore, as a silylating agent for silylation of secondary amines, there have been known a number of compounds including, for example, trimethylchlorosilane, N,O-bis(trimethylsilyl)acetamide (BSA) having the following formula:

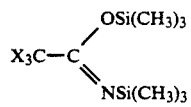

wherein X is a hydrogen atom or a fluorine atom, and the like.

Silylation of a secondary amine by use of trimethylchlorosilane, for instance, is carried out by reacting the secondary amine and trimethylchlorosilane in the presence of amines. The reaction can be expressed as follows:

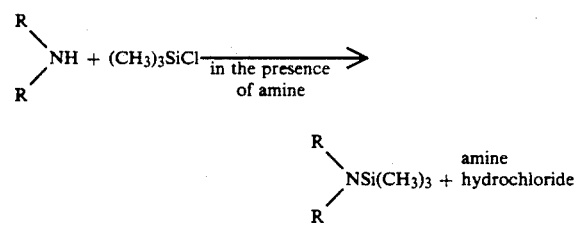

wherein R is a hydrocarbon group such as alkyl, etc.

As is clear from the reaction equation, the silylation of a secondary amine using trichlorosilane is accompanied by formation of amine hydrochlorides as by-product. Due to the chlorine contained in the amine hydrochloride, incorporation of the amine hydrochloride into the reaction product (silylated secondary amine) results in difficulty in using the reaction product as an electronics material, and the reaction product has an extremely limited use. The disposal of the by-produced amine hydrochloride raises another problem. Further, the silylation by use of trimethylchlorosilane has the drawback that the yield of the desired product is low.

Similarly, the silylation of a secondary amine by use of the above BSA is expressed as follows:

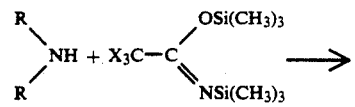

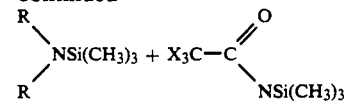

wherein R and X are as defined above.

As is clearly seen from the reaction equation, only one of the two trimethylsilyl groups contained in the BSA contributes to the silylation reaction. Thus, the BSA is not high in efficiency of silylation. Also, the use of BSA for silylation results in the formation of N-trimethylsilylacetamide or N-trimethylsilyltrifluoroacetamide as by-product. These silylacetamides are sublimable and are therefore very difficult to separate by distillation. Furthermore, the BSA itself readily decomposes at a temperature of about 120° C. under atmospheric pressure, and the use of the BSA as a silylating agent is greatly restricted accordingly.

SUMMARY OF THE INVENTION

It is an object of this invention to provide a silylating agent which enables silylation with high yield, ensures easy separation or removal of by-products of the silylation reaction and which is applicable to silylation in a wide range of temperature.

It is another object of this invention to provide a process for preparation of N,N-disubstituted aminotrialkylsilane through silylation of a secondary amine by use of said silylating agent.

According to this invention, there is provided a silylating agent comprising an N-(trialkylsilyl)benzanilide having the following general formula (1):

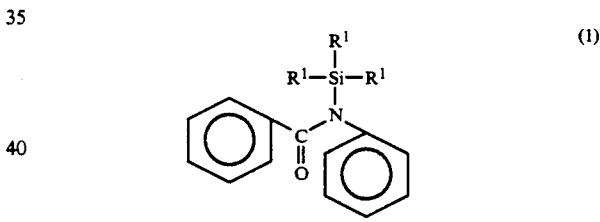

wherein $R^1$ may be the same or different from each other and each are a lower alkyl group of up to 4 carbon atoms.

According to this invention, there is also provided a process for preparing an N,N-disubstituted aminotrialkylsilane having the following general formula (3):

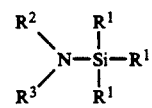

wherein $R^1$ is as defined above, and $R^2$ and $R^3$ may be the same or different from each other and each are a substituted or unsubstituted monovalent hydrocarbon group, the process comprising the step of reacting said silylating agent with a secondary amine having the following general formula (2):

wherein R² and R³ are as defined above.

DETAILED DESCRIPTION OF PREFERRED EMBODIMENTS

Silylating Agent

The silylating agent according to this invention comprises an N-(trialkylsilyl)benzanilide having the above general formula (1). The benzanilide is a known compound and has been used, for example, as a reactant in synthesis of amidoborane using a dialkylhalogenoborane [Refer to Z. Anorg. Allg. chem., 445, 122-8 (1978) and Monatsh. Chem., 110(1), 63-88 (1979)]. However, the use of the benzanilide as a silylating agent is not known.

In the above general formula (1), the lower alkyl groups R¹ of up to four carbon atoms include, for example, methyl, ethyl, n-propyl, isopropyl and n-butyl groups, etc., of which the methyl group is particularly preferred.

The silylating agent comprising an N-(trialkylsilyl)-benzanilide according to this invention is suitable for use in synthesis of N,N-disubstituted aminotrialkylsilanes as will be described below. In addition, the silylating agent of this invention is also applicable to, for example, protection of active hydrogen possessed by secondary amino groups, hydroxyl group, thiol group, carboxyl group, etc. It is possible to replace the active hydrogen with the trialkylsilyl group of the silylating agent, then to carry out various reactions and to thereafter carry out desilylation through hydrolysis, thereby introducing again an active hydrogen. Therefore, the silylating agent according to this invention is capable of being used extremely effectively for a variety of synthetic reactions. Particularly, the silylating agent of this invention is applicable to synthesis of compounds which are useful as a primer for photoresists in production of semiconductor devices, to synthesis of diverse medicines, and so on.

Synthesis of N,N-disubstituted aminotrialkylsilane

According to this invention it is possible to prepare an N,N-disubstituted aminotrialkylsilane having the above general formula (3) by reacting the aforesaid silylating agent with a secondary amine having the above general formula (2). The reaction is expressed as follows:

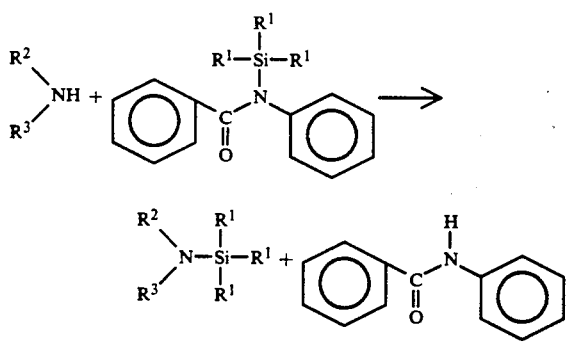

wherein R¹ to R³ are as defined above.

In the general formula (2) representing the secondary amine above, the substituted or unsubstituted monovalent hydrocarbon groups R² and R³ are preferably those which each have from 1 to 4 carbon atoms, for example, alkyl groups such as methyl, ethyl, n-propyl, isopropyl, n-butyl, etc., substituted alkyl groups such as chloromethyl, bromoethyl, trifluoropropyl, and so on.

In carrying out the above-described reaction, the silylating agent is preferably used in an amount of from 1 to 2 equivalents based on the secondary amine, more preferable amounts being from 1.1 to 1.4 equivalents. Where the amount of the silylating agent is excessively large, a large amount of unreacted silylating agent is left, with the undesirable result that much labor is needed to separate the unreacted silylating agent by distillation. If the amount of the silylating agent is too small, on the other hand, a large amount of unreacted secondary amine is left. Because the unreacted secondary amine generally has a low boiling point, the temperature of the reaction system falls in such situation, leading to low reaction rate and bad economy.

The reaction is preferably carried out at a temperature of from 50° to 200° C. If the temperature is excessively high, the silylating agent comes to decompose and the silylation reaction does not proceed effectively.

The duration of the reaction may be from about 8 to 15 hours.

After the reaction is finished, benzanilide formed as a by-product is removed by filtration. The benzanilide is a white solid matter having a melting point of from 163° to 165° C., and can be separated easily from the desired reaction product by a simple filter means, such as one using a glass filter. The benzanilide thus removed from the reaction product can be converted by a known method into N-(trialkylsilyl)benzanilide, to be used again for the process of this invention.

The filtrate obtained by the filtration as above is subjected to atmospheric distillation or the like, to give the intended N,N-disubstituted aminotrialkylsilane. The N,N-disubstituted aminotrialkylsilane thus obtained is of high purity.

According to the process of the invention, formation of amine hydrochloride or other similar chlorine-containing substances as by-products is obviated, as is clearly seen from the above reaction formula. It is therefore possible to avert effectively the disposal problem associated with such by-products and also the problem of limited use of the reaction product (N,N-disubstituted aminotrialkylsilane) due to contamination with such byproducts.

EXAMPLES

Example 1

A 100-ml four-necked flask equipped with a stirrer, a dry ice-methanol trap and a thermometer was charged with 20 g (0.074 mol) of N-(trimethylsilyl)benzanilide, and 3.6 g (0.080 mol) of dimethylamine was blown thereinto over 15 minutes to cause reaction at a liquid temperature of from 50° to 60° C. Next, the reaction solution was matured for 10 hours while the liquid temperature being kept at from 60° to 70° C. After the maturing was over, the reaction solution was filtered through a glass filter to remove benzanilides formed as a by-product. When the filtrate obtained by the filtration was subjected to atmospheric distillation, 6.8 g of dimethylaminotrimethylsilane was obtained as a distillate boiling at 86°-87° C. (Yield: 78%).

Example 2

A 100-ml four-necked flask equipped with a stirrer, a reflux condenser, a dropping funnel and a thermometer was charged with 20 g (0.074 mol) of N-(trimethylsilyl)- benzanilide, and 5.2 g (0.071 mol) of diethylamine was dropped thereinto through the dropping funnel over 15 minutes to cause reaction at a liquid temperature of from 50° to 70° C. Next, the reaction solution was matured for 14 hours while the liquid temperature being kept at from 70° to 80° C. After the maturing was over, the reaction solution was filtered through a glass filter to remove benzanilide formed as a by-product. When the filtrate obtained by the filtration was distilled at atmospheric pressure, diethylaminotrimethylsilane as a distillate boiling at 125°–126° C. was obtained in an amount of 8.1 g (Yield: 76%).

Example 3

A 100-ml four-necked flask equipped with a stirrer, a reflux condenser, a dropping funnel and a thermometer was charged with 20 g (0.074 mol) of N-(trimethylsilyl)-benzanilide, and 9.2 g (0.071 mol) of di-n-butylamine was dropped thereinto through the dropping funnel over 15 minutes to cause reaction at 50°–70° C.

After the dropping of di-n-butylamine was over, the reaction solution was matured for 12 hours by maintaining the temperature at 70°–80° C.

Subsequently, the reaction solution was filtered through a glass filter to remove benzanilide formed as a by-product, and the resulting filtrate was distilled under a reduced pressure. As a result, di-n-butylaminotrimethylsilane as a distillate boiling at 140°–143° C. under a pressure of 135 mmHg was obtained in an amount of 10.1 g (Yield: 71%).

We claim:

1. A process for preparing an N,N-disubstituted aminotrialkylsilane having the following general formula (3):

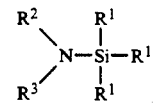

wherein $R^1$, $R^2$, and $R^3$ may be the same or different form each other and each is a lower alkyl group of up to 4 carbon atoms and $R^3$ may be the same or different form each other and each is a substituted or unsubstituted monovalent hydrocarbon group, the process comprising the step of reacting a silylating agent comprising an N-(trialkylsilyl)benzanilide having the following general formula (1):

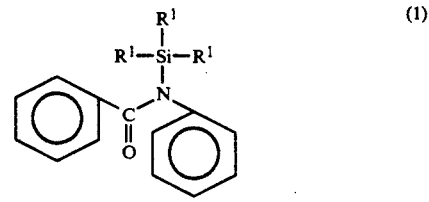

wherein $R^1$ is as defined above, with a secondary amine having the following general formula (2):

wherein $R^2$ and $R^3$ are as defined above.

2. The process according to claim 1, wherein $R^1$ is selected from the group consisting of methyl, ethyl, N-propyl, isopropyl and N-butyl.

3. A process according to claim 2, wherein $R^1$ is methyl.

4. The process according to claim 1, wherein the reaction is carried out at form 50° to 200° C.

5. A process according to claim 1, wherein $R^2$ and $R^3$ have from 1–4 carbon atoms and each may be the same or different and each is selected from the group consisting of methyl, ethyl, N-propyl, isopropyl, N-butyl, chloromethyl, bromoethyl, trifluoropropyl.

* * * * *